(12) United States Patent
Chavdar et al.

(10) Patent No.: US 8,024,961 B2
(45) Date of Patent: Sep. 27, 2011

(54) SIMULTANEOUS NORMAL AND RADIAL LIQUID PERMEAMETER

(75) Inventors: Bulent Chavdar, Rochester Hills, MI (US); Gregory Heeke, Wooster, OH (US)

(73) Assignee: Schaeffler Technologies GmbH & Co. KG, Herzogenaurach (DE)

( * ) Notice: Subject to any disclaimer, the term of this patent is extended or adjusted under 35 U.S.C. 154(b) by 504 days.

(21) Appl. No.: 12/291,612

(22) Filed: Nov. 12, 2008

(65) Prior Publication Data
US 2009/0139309 A1 Jun. 4, 2009

Related U.S. Application Data

(60) Provisional application No. 61/003,106, filed on Nov. 14, 2007.

(51) Int. Cl.
*G01N 15/08* (2006.01)
(52) U.S. Cl. .................................. 73/38; 73/37
(58) Field of Classification Search ............... 73/37, 38
See application file for complete search history.

(56) References Cited

U.S. PATENT DOCUMENTS

| | | | | |
|---|---|---|---|---|
| 2,348,985 A * | 5/1944 | Lewis | | 73/38 |
| 2,880,609 A * | 4/1959 | Byrkett et al. | | 73/38 |
| 2,923,148 A * | 2/1960 | Kirkham et al. | | 73/86 |
| 3,433,056 A * | 3/1969 | Nyffenegger et al. | | 73/38 |
| 3,466,925 A * | 9/1969 | Langlois et al. | | 73/38 |
| 3,577,767 A * | 5/1971 | Stedile | | 73/38 |
| 3,636,751 A * | 1/1972 | Pasini et al. | | 73/38 |
| 4,311,037 A * | 1/1982 | Gotchel et al. | | 73/38 |
| 4,531,404 A * | 7/1985 | Phelps et al. | | 73/38 |
| 4,679,422 A * | 7/1987 | Rubin et al. | | 73/38 |
| 4,791,822 A * | 12/1988 | Penny | | 73/865.6 |
| 5,535,616 A * | 7/1996 | Bors et al. | | 73/38 |
| 5,844,136 A * | 12/1998 | Marsala et al. | | 73/38 |
| 5,979,223 A * | 11/1999 | Fleury | | 73/38 |
| 6,021,661 A * | 2/2000 | Lowell et al. | | 73/38 |
| 6,178,808 B1 * | 1/2001 | Wang et al. | | 73/38 |
| 6,298,711 B1 * | 10/2001 | Volfkovich et al. | | 73/38 |
| 6,401,523 B1 * | 6/2002 | Fernandes et al. | | 73/38 |
| 6,655,192 B2 * | 12/2003 | Chavdar | | 73/38 |
| 6,948,354 B1 * | 9/2005 | Chen et al. | | 73/38 |
| 7,059,175 B2 * | 6/2006 | Volfkovich et al. | | 73/38 |
| 7,178,384 B2 * | 2/2007 | Bujas et al. | | 73/38 |
| 7,412,875 B2 * | 8/2008 | Zornberg et al. | | 73/38 |
| 7,882,726 B2 * | 2/2011 | Gupta et al. | | 73/38 |
| 2002/0095984 A1 * | 7/2002 | Johnson | | 73/152.05 |
| 2002/0178790 A1 * | 12/2002 | Swersey et al. | | 73/38 |
| 2005/0103094 A1 * | 5/2005 | Knight et al. | | 73/38 |
| 2005/0229682 A1 * | 10/2005 | Gupta et al. | | 73/38 |

* cited by examiner

*Primary Examiner* — David A. Rogers
(74) *Attorney, Agent, or Firm* — Davidson, Davidson & Kappel, LLC

(57) ABSTRACT

A permeameter including a fluid control chamber, a permeability specimen area, and a first outlet from the specimen area measuring fluid as a function of a normal permeability of at least one specimen in the specimen area and a second outlet from the specimen area receiving and measuring further fluid as a function of a radial permeability of the at least one specimen in the specimen area.

15 Claims, 2 Drawing Sheets

SIMULTANEOUS NORMAL AND RADIAL LIQUID PERMEAMETER

Priority to U.S. Provisional Patent Application Ser. No. 61/003,106, filed Nov. 14, 2007, is claimed, the entire disclosure of which is hereby incorporated by reference herein.

The present invention relates generally to the permeability measurements of wet friction materials for wet clutch applications.

BACKGROUND

U.S. Pat. No. 6,655,192, hereby incorporated by reference herein, describes a permeameter providing both normal and lateral permeability measurements on porous materials. The prior art permeameter has a base, a fluid chamber housing and a compression ring. The base has a recess. The recess is defined by a transverse wall and a cylindrical upper sidewall. The fluid chamber housing has an upper axially extending tubular section and an enlarged lower section. A piston is positioned within the upper tubular section which is axially moveable within the upper tubular section. A seal is provided between the head of the piston and the upper tubular section with an o-ring.

SUMMARY OF THE INVENTION

An object of the present invention provides a permeameter including a fluid control chamber, a permeability specimen area, and a first outlet from the specimen area measuring fluid as a function of a normal permeability of at least one specimen in the specimen area and a second outlet from the specimen area receiving and measuring further fluid as a function of a radial permeability of the at least one specimen in the specimen area.

An object of the present invention includes the simultaneous measurement of normal permeability and lateral permeability of porous materials with equal flow path and equal cross-sectional flow area in each test direction with the same test fluid using a stand alone permeameter with constant compression force on the test specimen.

BRIEF DESCRIPTION OF THE DRAWINGS

Further features and advantages of the invention will become apparent from the following detailed description taken in conjunction with the accompanying drawing, in which.

DETAILED DESCRIPTION

Figure 1:
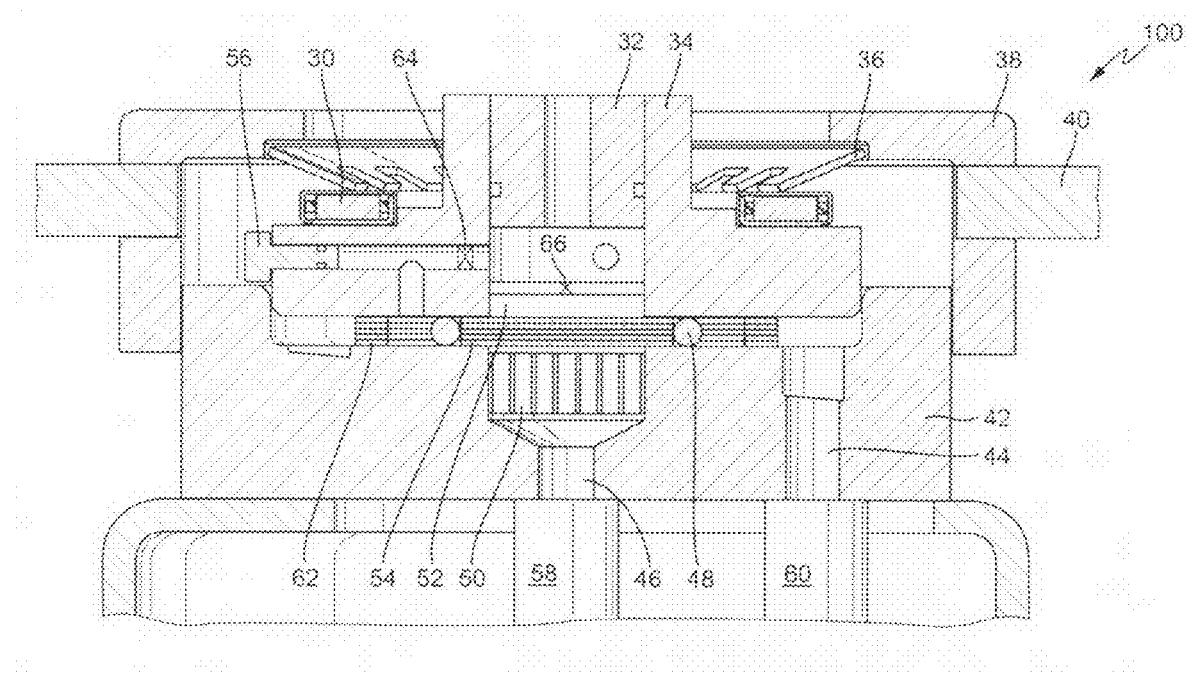
FIG. 1 illustrates one embodiment of a permeameter according to the present invention.

Fluid flow through a porous media can be measured using a permeameter. However, the pore structure of paper based wet friction materials is anisotropic, hence permeability depends on the direction in which fluid flows through the material. The liquid permeability of wet friction materials needs to be measured in normal and radial directions with oil. The normal and radial permeability measurements are done sequentially in the current state of the art. Comparison of normal and radial permeability measurements with sequential measurements is inadvertently affected by the change in room temperature which affects the viscosity of fluid and by the repeatability of the loading mechanism of the test machine from test to test in the current state of the art.

The fluid flow paths through a normal permeability test specimen and a radial permeability test specimen are not equal in the current state of the art. Typically, the flow path is 10 to 20 times shorter in a normal permeability test than in a radial permeability test in the current state of the art. Therefore a radial permeability test lasts 10 to 20 times longer than a normal permeability test when the tests are run with the same fluid. In order to shorten the test time, radial permeability tests are typically run with water (low viscosity fluids) while normal permeability tests are run with oil (high viscosity fluid) in the current state of the art with an assumption that permeability measurements will not be affected by the chemistry of fluids, which may not always be true.

The specimens cross sectional area perpendicular to the fluid flow is also different in the normal permeability test and in the radial permeability test in the current state of the art. Cross sectional area is 8.6 times larger in the normal permeability test than in the radial permeability tests in the current state of the art. Hence, normal permeability test results are averaged over a larger area than the radial permeability test results in the current state of the art causing different levels of accuracies in each measurement due to the inherent inhomogeneity of most wet friction materials.

Comparison of normal and radial permeability values becomes difficult if the measurements are done at two different lengths of flow path, on two different cross sectional areas and two different fluid systems in the current state of the art.

Furthermore, the current state of the art is not a stand alone unit and requires a universal testing machine to compress the test specimen and to force the fluid flow through the specimen. Compression of the test specimen and compression of the test fluid are done sequentially with increased test setup time and added complexity. The current state of the art performs compression of the test specimen as follows: after the test specimen is compressed by the apply shaft of the universal test machine, the compression displacement is fixed by a compression ring and the apply shaft of the universal test machine is freed for the next task which is compression of the test fluid. However, due to viscoelasticity, the test specimen goes through relaxation, meaning that the compression force does not stay constant while the compression displacement stays constant on the test specimen. The universal testing machines are typically much more expensive than the permeameter itself and require a substantial capital investment.

FIG. 1 shows one embodiment of a permeameter according to the present invention. Permeameter 100 has a holey block 50 and a fluid chamber 52 with a piston 32. Fluid chamber 52 supplies pressurized test fluid for both the normal and radial permeability measurements simultaneously. Piston 32 is enclosed by a cylinder and upper platen 34. Mounted on cylinder and upper platen 34 is a bearing 30. Attached to bearing 30 is a diaphragm spring 36. Diaphragm spring 36 and a frictionless loading mechanism provide constant compression force to normal and radial test specimens simultaneously. Spring 36 may be a Belleville spring. Attached to holey block 50 is an outlet 46 used to drain the fluid into a graduated cylinder or flowmeter 58 to measure the normal fluid flow. An outlet 44 is attached to another graduated cylinder or flowmeter 60 used to measure the radial fluid flow independently of the normal fluid flow. Connected to fluid chamber 52 is a plug 56. In between fluid chamber 52 and holey block 48 are a ring 62 and a disk 54. In between ring 62 and disk 54 is a seal 48, which separates the normal permeability test specimen compartment from the radial permeability test specimen compartment. Cylinder and upper platen 34 is connected to a lower platen 42 by a cap 38. In between cylinder and upper platen 34 and lower platen 42 can be an o-ring seal groove. Handles 40 are engaged to cap 38.

Permeameter 100 also can have on/off valves 64, 66, for example, enabling the running of the normal and radial permeability tests individually. If both valves are open, simultaneous testing can occur. If valve 64 is closed and 66 open, a normal test can be run individually. If valve 64 is open and 66 closed, the radial test may be run individually. On/off valves and/or seals can also be located so that the normal and radial permeability tests can be run on the same disk specimen sequentially. Attachments may be added to the permeameter to measure the Joseph and Beaver slip coefficients of the porous test specimen.

Permeameter 100 can also be configured without piston 32 and piston cylinder 34. A pressurized oil source can be used to introduce fluid into the fluid chamber, in place of the piston and piston cylinder, with all other aspects of the apparatus remaining the same.

Figure 2:
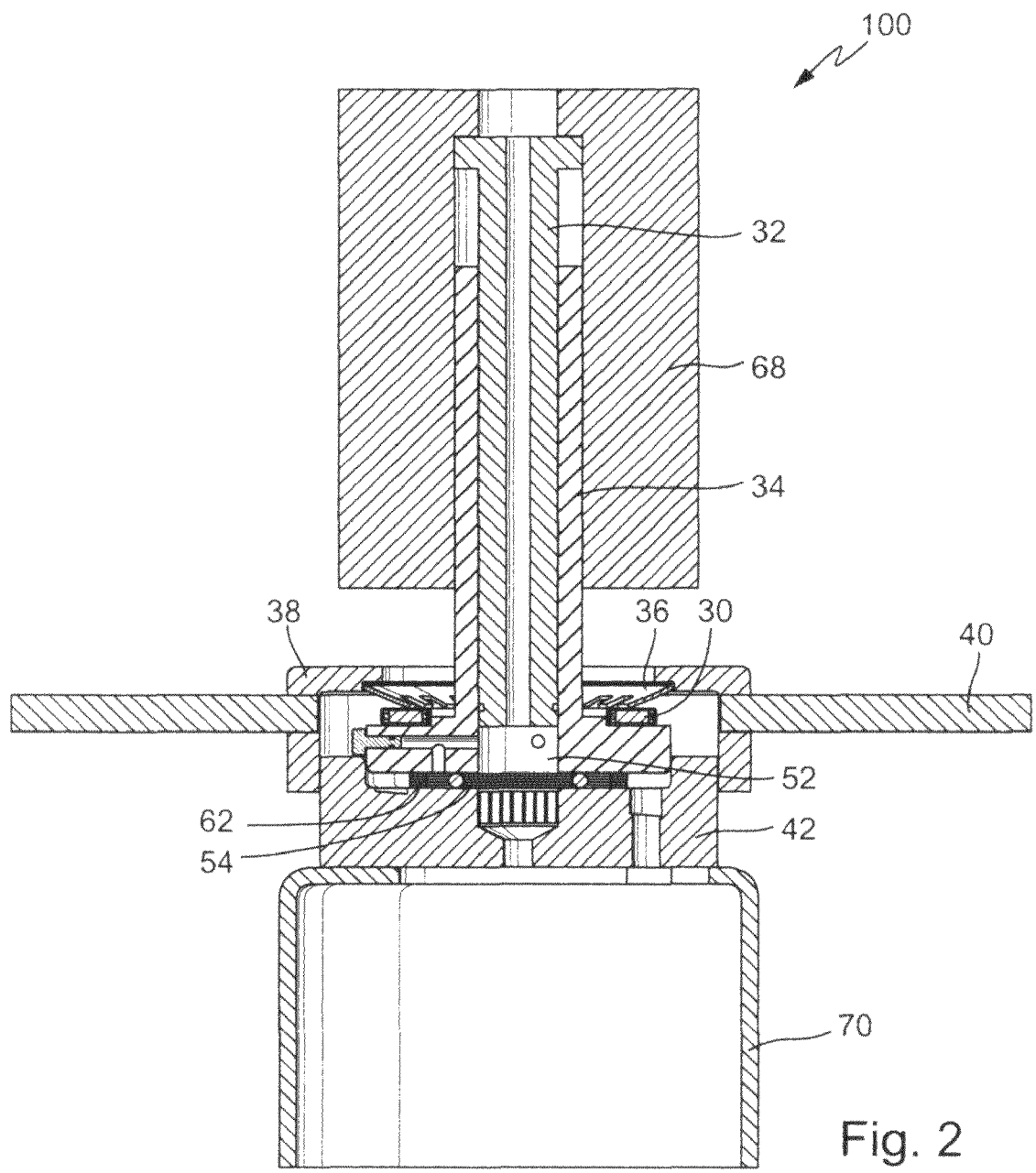
FIG. 2 illustrates a perspective view of the present invention.

FIG. 2 shows the enlarged view of the present invention. Piston 32 is enclosed by cylinder and upper platen 34 and deadweight 68. Deadweight 68 loads integrated with piston 32 of the stand alone permeameter to apply constant pressure on the test fluid. At the end of piston 32 is fluid chamber 52. Below fluid chamber 52 are disk 54 and ring 62. Mounted on cylinder and upper platen 34 are bearings 30. Attached to bearing 30 is diaphragm spring 36. Cylinder and upper platen 34 connects with cylinder and lower platen 42 via cap 38. Engaged with cap 38 are handles 40. Permeameter 100 is mounted via mounting 70.

Figure 3:
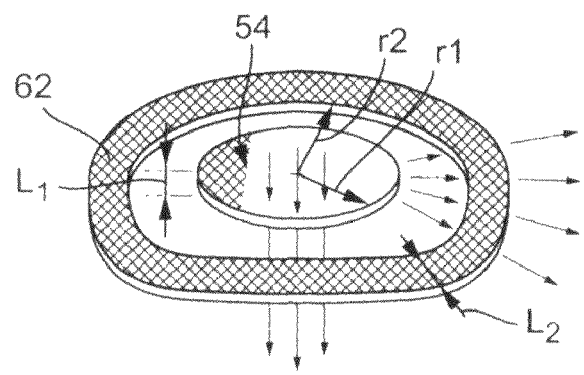
FIG. 3 illustrates a geometrically optimized disk and ring specimen used in a permeameter of the present invention.

FIG. 3 shows a perspective view of a geometrically optimized ring and disk specimen used in the permeameter according to the present invention. Ring 62 surrounds disk 54. r1 is the radius of disk 54 and r2 is the inner radius of ring 62. Geometrically optimized disk 54 and ring 62 test specimens can be comparable if the following relations are satisfied:

$$A1=A2 \quad (1)$$

$$L1=L2 \quad (2)$$

$$r1<r2 \quad (3)$$

where A is the specimen area perpendicular to the fluid flow. L1 is the thickness of disk 54 and ring 62 and L2 is the width of annulus of ring 62.

For example, assuming the friction material is 1 mm thick and the width of the annulus of ring 62 is 5 mm. Then if 5 layers of material are stacked in for disk 54 and ring 62 in one test, the equation (2) is satisfied:

$$L1=L2=5 \text{ mm}$$

Equation (2) requires:

$$\pi*r1^2=2*\pi*r2*L1$$

Since L1=5 mm $$r1*r1=10*r2$$

Finally, the inequality of (3) provides final dimensions:
if r1=15 mm, then r2=22.5 mm
or if r1=17 mm, then r2=28.9 mm, etc.

In the above example, disk 54 and ring 62 specimens are created by stacking up 5 layers of 1 mm thick friction material. If the thickness of one layer of friction material is 5 mm, then only one layer of material is needed to make disk 54 and ring 62 specimens. In the above example, the dimensions were selected to be reasonable with the current state of manufacturing processes. However, the dimensions of disk 54 and ring 62 specimens are not limited to the dimensions used in the example, provided the mathematical relationships are used.

Interactions of normal and radial permeability of wet friction materials affect the friction performance of wet friction materials. Formulation and development of superior wet friction materials is possible if the normal and radial permeability are measured simultaneously. Simultaneous measurement of normal and radial permeability values with the same test fluid is needed for accurate comparison of normal and radial permeability of wet friction materials. A stand alone permeameter with dead weights negates the need for a universal testing machine to actuate the permeameter and provides an economical solution. Hence, the current invention provides a unique solution to simultaneous measurement of normal and radial permeability. Furthermore, the application of simultaneous normal and radial liquid permeametry is not limited to wet friction material but can be applied to any porous materials which have three dimensional structural integrity.

What is claimed is:

1. A permeameter comprising:
   a fluid control chamber;
   a permeability specimen area; and
   a first outlet from the specimen area coupled to a first measuring device measuring fluid as a function of a normal permeability of at least one specimen in the specimen area and a second outlet from the specimen area coupled to a second measuring device receiving and measuring further fluid as a function of a radial permeability of the at least one specimen in the specimen area.

2. The permeameter device as recited in claim 1 further comprising a piston and a piston cylinder.

3. The permeameter device as recited in claim 2 wherein the piston is integrated with deadweight.

4. The permeameter device as recited in claim 2 wherein a bearing is connected to the piston cylinder.

5. The permeameter device as recited in claim 4 further comprising a diaphragm spring mounted on the bearing.

6. The permeameter device as recited in claim 5 wherein the diaphragm spring is a Belleville spring.

7. The permeameter device as recited in claim 1 further comprising a mount.

8. The permeameter device as recited in claim 1 wherein the specimen area further comprises a ring specimen area and a disk specimen area.

9. The permeameter device as recited in claim 1 further comprising a seal between the ring specimen area and the disk specimen area.

10. The permeameter device as recited in claim 1 further comprising a first flow measurer connected to the first outlet and a second flow measurer connected to the second outlet.

11. The permeameter device as recited in claim 10 where in the first flow measurer is a graduated cylinder.

12. The permeameter device as recited in claim 10 wherein the first flow measurer is a flowmeter.

13. The permeameter device as recited in claim 1 further comprising on/off valves enabling the running of individual normal and radial permeability tests.

14. A method for measuring the permeability of at least one specimen comprising:
   providing the apparatus as recited in claim 1; and
   measuring a normal and radial permeability of the at least one specimen simultaneously.

15. The method as recited in claim 14 wherein at least one specimen includes a ring and a disk specimen.

* * * * *